(12) United States Patent
Cook et al.

(10) Patent No.: US 6,730,230 B2
(45) Date of Patent: *May 4, 2004

(54) USE OF HIGH DENSITY MICROPARTICLES FOR REMOVAL OF PATHOGENS

(75) Inventors: David N. Cook, Lafayette, CA (US); Rodney L. Monroy, Rockport, MA (US)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 116 days.

This patent is subject to a terminal disclaimer.

(21) Appl. No.: 10/043,471

(22) Filed: Jan. 11, 2002

(65) Prior Publication Data

US 2002/0117453 A1 Aug. 29, 2002

Related U.S. Application Data

(60) Provisional application No. 60/262,443, filed on Jan. 16, 2001.

(51) Int. Cl.$^7$ .............................. B03C 1/00; G01N 33/53; G01N 33/569
(52) U.S. Cl. ................. 210/695; 210/800; 210/222; 252/62.51 R; 435/5; 435/7.2; 435/7.32; 435/261; 436/523; 436/526
(58) Field of Search .................. 210/695, 800, 210/222; 252/62.51 R; 435/5, 7.2, 7.32, 261; 436/523, 526

(56) References Cited

U.S. PATENT DOCUMENTS 3,970,518 A * 7/1976 Giaever ................... 435/7.32
5,576,185 A * 11/1996 Coulter et al. ............. 210/695

* cited by examiner

Primary Examiner—David A. Reifsnyder
(74) Attorney, Agent, or Firm—Elliot M. Olstein; Raymond E. Stauffer

(57) ABSTRACT

Methods of using high-density microparticles to bind and remove pathogens from biological fluids are disclosed. Pathogens include prions, viruses, bacteria and protozoa.

28 Claims, No Drawings

USE OF HIGH DENSITY MICROPARTICLES FOR REMOVAL OF PATHOGENS

This application claims the benefit of priority of provisional application Ser. No. 60/262,443, filed Jan. 16, 2001, the contents of which are incorporated herein by reference in their entirety.

TECHNICAL FIELD

This invention relates to methods for separating and isolating pathogens from biological fluid samples such as blood and blood components by means of high density microparticles.

BACKGROUND

Whole blood includes cellular (erythrocytes or red blood cells, leukocytes or white blood cells, thrombocytes or platelets) along with non-cellular components (plasma). When blood is collected from a donor for use, the whole blood is typically separated by centrifugation into such components, which can then be used therapeutically, rather than administering whole blood, in order to maximize the clinical and economic utility of blood. The leukocytes present in whole blood are often carried during processing into each of the blood components. Leukocytes may transmit infectious agents, such as cell-associated viruses (e.g. cytomegalovirus or human immunodeficiency virus) or they may cause adverse immunological reactions, such as alloimmunization. For those reasons, leukocyte removal is often desirable and several methods have been developed to remove leukocytes without causing appreciable damage to the blood or blood component. See for example, Coulter, et al., U.S. Pat. No. 5,576,185 and Pall, et at., U.S. Pat. No. 5,229,012.

However, other pathogenic substances may still be present in whole blood or its various components, that can be harmful to a patient receiving such blood. This is of particular concern when the patient is immune compromised and more susceptible to pathogens that may be present in the blood. Such pathogens include viruses, protozoa and bacteria. In addition, more recently, concern has arisen over prions, which are protein agents believed to be capable of transmitting spongiform neuropathies such as Creutzfeld Jacob's Disease. Experimental evidence in animals suggests that these agents may be transmitted by blood transfusions (Houston et al., Lancet 356(9234): 999–1000, 2000), and concern over transmission of these agents has resulted in recall of some human blood-derived products.

Although substantial removal of some pathogens such as cell-associated viruses may occur during leukocyte removal, there is a continuing need to develop more quantitative and broader methods of removing such pathogens from whole human blood and blood components, while maintaining the integrity of the blood.

One method of eliminating pathogens is by inactivation, for example, by directly or indirectly inhibiting the virus's ability to replicate. Reichl, U.S. Pat. No. 5,633,349 describes the inactivation of prions, viruses and other infectious agents by treatment with a chaotropic agent such as urea or sodium thiocyanate. Use of a chaotropic agent for treatment of blood cells has the undesired consequence of destroying the therapeutic utility of the resulting cellular product. Miekka, et at., U.S. Pat. No. 6,106,773 relates to the use of an iodinated matrix to disinfect biological fluids by inactivating pathogens contained therein. Cook et at., PCT/US98/00532 describes the use of frangible compounds for chemical inactivation of pathogens by targeting nucleic acids. Other inactivation methods use photoactivation, which is a combination of a photochemical agent and light. Such agents include psoralens (Lin, et at., U.S. Pat. No. 5,459,030), methylene blue (Wolf, Jr., et at., U.S. Pat. No. 5,527,704) and phthallocyanines (Horowitz, et at., U.S. Pat. No. 5,637,451).

Inactivation is not uniformly successful in eliminating pathogens since some are not susceptible to inactivation under conditions that preserve the therapeutic or diagnostic usefulness of a biological fluid. The Hepatitis A virus is a small non-enveloped, blood borne virus that resists inactivation by detergents, heat and most small-molecule chemical and photochemical inactivating agents. Prions are another example of a pathogen that resists inactivation by almost all forms of sterilizing treatment, including heat, ionizing radiation, and chemical treatments. In particular, because prions lack nucleic acids and form an extraordinarily stable protein structure, they are generally resistant to practical methods of inactivation. For agents such as these, a removal method that also preserves the therapeutic or diagnostic utility of the biological fluid is clearly desirable.

Methods of removing pathogens also include physical separation techniques such as by filtration or chromatography. Wick, et at., U.S. Pat. No. 6,051,189 relates to the detection and extraction of submicron particles such as viruses and prions, by centrifligation and ultrafiltration. Gawry, et al., U.S. Pat. No. 5,808,011 describes a method of prion removal using an anion exchange chromatographic column under conditions that cause a gradient elution.

Physical separation techniques often use magnetic particles. For example, Giaever, et at., U.S. Pat. No. 3,970,518 describes the use of antibody-coated magnetic particles to separate select cells, bacteria or viruses from multi-cell, bacteria or virus populations. Magnetic particles are available in various sizes and can be either non-uniform (Josephson, U.S. Pat. No. 4,672,040) or very uniform (Homes, et at., U.S. Pat. No. 5,512,439). Magnetic particles are generally <4.5 $\mu$m in diameter and have a density of <1.8 g/cm$^3$. The magnetic microspheres are intended to be maintained in suspension in the sample and consequently are designed not to settle by gravity.

Non-magnetic, physical separation methods have also been used to separate various cell components from samples of whole blood or bone marrow. Coulter, et at., U.S. Pat. No. 5,576,185, describes the use of reactant-coated, high density microparticles that separate under gravity, a mechanism that allows for separation of undesired cells without substantially physically damaging the blood cells. The advantages of high density microparticles over magnetic particles in the area of cell separation are well established. However, until now, no one has attempted to apply this technology for removal of cellular pathogens such as viruses, bacteria and non-cellular pathogens such as prions.

SUMMARY OF THE INVENTION

The invention provides a novel method for separating pathogens from a biological fluid sample. A plurality of high density microparticles ("HDM") having a reactant such as an anti-pathogen antibody, bound thereto are mixed with the sample. The HDM, with the pathogen bound thereto, are allowed to differentially settle by gravity and the remaining sample is removed.

One aspect of the invention pertains to a method of removing at least one population of target pathogens from a biological fluid sample, comprising: providing a plurality of high density microparticles having bound thereto a reactant which specifically binds to the target pathogen, and having a density sufficient to provide differential gravity settling of the target pathogen from the sample; mixing a portion of the sample with the microparticles to bind the microparticles to the target pathogen; settling the microparticles with the bound pathogen in the sample to produce a supernatant substantially free from the bound pathogen, where the settling is accomplished primarily by gravity; and separating the microparticles bound to the pathogen from the supernatant.

DESCRIPTION OF THE INVENTION

Definitions

The term "high density microparticles" or "HDM" is used to mean particles having a density greater than that of the non-target materials present in the sample, so that the HDM are able to settle out of the sample by differential gravity, i.e., the HDM will settle more rapidly than the non-target materials. Typical "non-target" materials include red blood cells or white blood cells, platelets, plasma proteins and so forth. Clearly, the greater the differences in density between the HDM and the non-target materials present in the sample, the faster the differential settling will occur. Preferably the particles have a density of at least twice, more preferably 2 or 3 times the density of the non-target materials present in the sample. In particular, HDM preferably have a density greater than 2 g/cm$^3$, typically on the order of 7–10 g/cm$^3$. Preferably the HDM are nickel, which has a density of about 9 gm/cm$^3$.

The term "sample" is intended to mean the substance to be analyzed or used therapeutically, where the substance is either a fluid itself or is suspended in a fluid medium. The sample is typically a biological fluid, which includes by means of illustration and not limitation, whole blood or a component thereof such as plasma, a platelet-enriched blood fraction, a platelet concentrate or packed red blood cells; cell preparations such as dispersed tissue, bone marrow aspirates or vertebral body bone marrow; cell suspensions; urine, saliva and other body fluids; bone marrow; spinal fluid; and so forth. The sample can also be a lysed preparation, such as cell lysates, which can be formed using known procedures such as the use of lysing buffers, and so forth. The volume of the sample used in the methods of the invention will vary depending upon the particular application. For example, when the method is being used for a diagnostic or research application, the volume of the sample will typically be in the microliter range, and can be 10 μl or greater. When the method is being used for a therapeutic application such as for clinical transplantations, the volume of the sample will typically be in the milliliter to liter range, for example, 100 milliliters to 3 liters. In an industrial application, such as purification of pooled donor plasma, the volume may be tens of thousands of liters.

The term "pathogen" is intended to include any biological organism that is harmful to humans and includes, by way of illustration and not limitation, non-cellular pathogens such as prions, including classical CJD and new variant CJD; protozoa such as giardia; viruses such as Human Immunodeficiency Virus, Herpes Simplex Virus, Epstein Barr Virus, cytomegalovirus, T-cell lymphotrophic virus, varicella zoster virus, adenovirus, Hepatitis A virus, Hepatitis B virus, Hepatitis C virus, human B-19 parvovirus, Nipah virus, hantaviruses, yellow fever virus (family Flaviviridae or Flavivirus) the tick-borne hemorrhagic fever viruses, or the tick-borne encephalitis viruses; cellular pathogens such as bacteria, which include, for example, streptococcus, diptheria, mycobacterium, treponema, *Yersinia enterocolitica, Klebsiella pneumoniae, Pseudomonas aerugonisa, Staphylococcus, aureus, Bacillus anthracis* (causative agent of anthrax), *Clostridium botulinum* and its toxins (causative agents of botulism), *Yersinia pestis* (causative agent of plague), *Variola major* (causative agent of smallpox), *Francisella tularensis* (causative agent of tularemia), *Coxiella burnetti* (causative agent of Q fever), bacteria of the genus Brucella (causative agents of brucellosis) *Burkholderia mallei* (causative agent of glanders), *Ricinus communis* and its toxins, *Clostridium perfringens* and its toxins, such as the epsilon toxin, Staphylococcus toxins, such as enterotoxin B, bacteria which cause multidrug resistant tuberculosis such as drug-resistant *Mycobacterium tuberculosis* strains, or other pathogenic bacteria known to be transmitted by biological fluids; fungi such as such as candida; and parasites such as plasmodium, ascaris, leishmania, and *Trypanosoma cruzi*. The term "target pathogen" refers to the pathogen of interest that is to be removed from the sample.

The term "pathogen removal" means the substantial reduction of the number of pathogenic particles from a biological fluid as measured by a biological, chemical or physical titration assay. Pathogen removal is usually measured as a logarithmic function, for instance a 1-log removal indicates that starting titer of the pathogen has been reduced by 90%. A 2-log removal indicates a reduction by 99%, and so on. Substantial reduction of a pathogen can include removal of 1- to 3-logs or greater, and preferably results in greater than 4- to 5-logs of removal or a final titer below the limit of detection of the pathogen assay. Pathogen detecting assays include physio-chemical assays, for instance a fluorescence assay, or biochemical assays, for instance an ELISA assay. Pathogen detecting assays may involve the in vitro use of cells such as viral plaque assays or microbial growth assays. For some pathogens, the only appropriate endpoint is an in vivo titration assay since the pathogen only replicates in a particular host animal. These and other methods known to those in the art may be used for measuring pathogen removal.

The present invention is based on the finding that high density microparticles ("HDM") offer advantages over other solid supports, primarily magnetic particles, for the removal of pathogens from biological fluids. While not being limited to a particular mechanism, the density of the HDM is such that during mixing, the HDM contact the target pathogen in the sample at rates greater than by classical diffusion because the particles are moving through the solution under the influence of gravity, thus leading to the need for significantly fewer particles than used in state of the art methods, and more effective and rapid mixing. This results in a more cost-effective reagent and significantly lower non-specific binding due to the lower surface area. "Surface area" refers to the area of the particle surface available for reaction, and fewer particles translates to lower surface area per reaction.

Additional advantages of the instant invention include: rapid reaction kinetics (speed of target pathogen capture), lack of requirement for ancillary devices such as a magnetic separator, simplicity of rinsing and adding of reagents and of particle separation, and economy of reagents because the speed of capture is such that significantly fewer particles are required than with magnetic separation as noted above. Further, the use of gravity settling to separate the particles is far less vigorous and time consuming than traditional separation techniques such as centrifugation which generates shear forces, which can degrade desirable materials present in the biological fluid.

A further advantage of the method of the invention is that the method does not cause substantial cell damage and preserves the function of the sample. This is of particular concern when the sample is a biological fluid such as whole blood or a component thereof which is intended for therapeutic use. Preservation of function can be assessed readily based on the intended use by one skilled in the particular art and accepted medical practice defines a large range of cellular, biochemical and physical properties of blood cells that are therapeutically acceptable. For instance, regulatory standards of product approval recognize that blood cells with far less than 100% activity may be therapeutically useful. For instance, 24-hour post transfusion recovery of red blood cells as low as 70% after processing and storage has been deemed an acceptable value for therapeutic use. After depletion of pathogens in a red blood cell suspension, the function of the red blood cells can be measured using standard in vitro methods, including hemolysis, ATP levels, cellular deformability and pH. The functionality of red blood cells can also be measured in vivo by determining the 24-hour post-transfusion recovery in human subjects. Similarly, platelet recoveries 24-hour post transfusion of 30–50% are considered routine and acceptable in transfusion medicine. Platelet function can be measured by standard in vitro tests including aggregation assays, pH, shape change, osmotic shock and morphology, as well as by in vivo determination of the 24-hour post transfusion recovery. Hematopoietic stem cells can be enumerated via flow cytometry and their viability determined by dye exclusion methods, and their proliferative potential by colony-forming assays.

The present invention relates to methods of using high density microparticles ("HDM") to separate or isolate target pathogens by gravity sedimentation. In one embodiment of the invention, the HDM are first added to the sample in a mixing step. Following the mixing step, the sample is simply stood on end and the HDM bound to the target pathogen, settle out by gravity, typically over a one to four minute time period. A unique feature of the methods of the invention is that the gentle settling of the HDM by gravity is such that the fluid is pushed aside by the falling HDM thus eliminating non-specific trapping of undesired materials and other cellular components by the HDM. This represents a significant improvement over use of magnetic particles where nonspecific trapping occurs as the particles traverse through the fluid toward the magnet.

High Density Microparticles

The HDM can be made of numerous materials, including by way of illustration and not limitation, metals such as iron, nickel, aluminum, copper, zinc, cadmium, titanium, zirconium, tin, lead, chromium, manganese and cobalt; metal oxides and hydrated oxides such as aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. The microparticles can also be made of non-metal or organic materials such as cellulose, ceramics, glass, nylon, polystyrene, rubber, latex, and so forth. The microparticles can also be a combination of a metal and a non-metal or organic compound, for example, methacrylate or styrene coated metals and silicate coated metals. The base material may be doped with an agent to alter its physical or chemical properties, for instance the inclusion of rare earth oxides in aluminosilicate glasses to create a paramagnetic glass materials with high density (White and Day (1994) *Rare Elements in Glasses*, Key Engineering Materials Vol. 94–95:181–208.)

Suitable commercially available HDM, include for example, nickel (Type 123, VM 63, 18/209A, 10/585A, 347355 and HDNP sold by Novamet Specialty Products, Inc., Wyckoff, N.J.); 08841R sold by Spex, Inc.; 01509BW sold by Aldrich), stainless steel (P316L sold by Ametek), zinc dust (Aldrich), palladium (D13A17 sold by John Matthey Elec.), $TiO_2$, $SiO_2$ or $MnO_2$ (Aldrich).

As noted above, the HDM have a density of at least twice, more preferably 2 or 3 times the density of the non-target materials present in the sample. In this manner, the HDM are designed to settle under gravity and thus be separated them from the non-target materials. For example, the non-target materials commonly include blood cells, which have a density on the order of 1.05 gm/cc. Therefore, for the preferred methods of the invention, the HDM should be substantially more dense than the blood cells, e.g., as stated above, on the order of 2–3 times more dense than the blood cells.

The configuration of the HDM can vary from being irregular in shape to being spherical, from having an uneven or irregular surface to having a smooth surface, and can be finely divided powders or ultrafine particles. The particle size (nominal diameter) is not critical to the invention but will typically range from 1–50 $\mu$m, more typically 3–35 $\mu$m, and is preferably about 5 $\mu$m. The microparticles can be uniform in size or can vary in size with the average particle size preferably being in the aforementioned range.

The shape of the HDM also may be useful in that removal of a specific pathogenic protein in a mixed cellular-plasma fluid characteristic of blood, a spherical component moves through the fluid more efficiently, and minimizes entrapment of cellular components.

Size specificity also can be determined by the target pathogen, where cellular targets may be removed by particles which preferably are 1 to 5 microns in size.

In one embodiment, the HDM have a surface area of at least 0.4 $m^2/g$, preferably from about 0.4 $m^2/g$ to about 0.5 $m^2$g.

The preferred HDM are formed from carbonyl nickel, such as the nickel powders made by Novamet, a subsidiary of INCO, USA, as Nickel Powder Type 123. The microparticles are not uniform in size, but have a size range of 3–35 $\mu$m, with a nominal diameter of about 5 $\mu$m.

The aforementioned particle materials are intended to be illustrative only and are not intended to be limiting in any manner, since any particle material, along with any particle size or configuration, can be used as long as the microparticles settle by differential gravity as required by the invention.

The HDM are linked to a reactant and are preferably coated before being linked to the reactant. Numerous coatings as are well known in the art can be utilized, for example the microparticles can be coated with human serum albumin, tris (3-mercaptopropyl)-N-glycylamino) methane (Siiman, et at., U.S. Pat. No. 6,074,884), gelatin-aminodextrans (Siiman, et at., U.S. Pat. No. 5,466,609) or amino acid homopolymers or random copolymers. A preferred random amino acid copolymer is poly(glutamate, lysine, tyrosine) [6:3:1] obtainable from Sigma Chemical Co. as Product No. P8854. It is a linear random polymer of the amino acids glutamic acid, lysine, and tyrosine in a ratio of 6 parts glutamic acid, 3 parts lysine, and 1 part tyrosine. In another embodiment, the amino acid copolymer is an amino acid copolymer including lysine and tyrosine in a ratio of 4 parts lysine to 1 part tyrosine. In yet another embodiment, the amino acid copolymer is an amino acid copolymer including lysine and alanine in a ratio of 1 part lysine to 1 part alanine. Such coatings will be selected with a view to optimal reactivity and biocompatibility, according to the need of the biological fluid to be treated. Another suitable coating involves first coating the HDM with a synthetic polymer, and then activating the polymer prior to linkage with the reactant. For example, the HDM can have a thin coating of hydrated silica ("silicate") or a silicate derivative, obtained by a process referred to as "silanolization" which uses sodium metasilicate and ammonium acetate. An aqueous solution of sodium/metasilicate is formed, ammonium acetate is added, followed by the addition of the particles to be coated.

It may be desirable to pre-treat the microparticles prior to coating. Such pre-treatment of the nickel microparticles serves to sterilize and depyrogenate and also creates an oxide layer on the particle surface. Typically, such pre-treatment involves heating the nickel microparticles for about 2–6 hours, preferably for about 5 hours, at a temperature within the range of about 200–350° C., preferably about 250° C. This pretreatment is particularly beneficial when metallic microparticles are used.

Reactants

The reactant is a molecule capable of binding with the requisite affinity and specificity to the target pathogen. Suitable reactants include monoclonal and polyclonal antibodies (including antibody fragments) that specifically bind to the target pathogen, or synthetic molecules designed or selected to have high affinity for target pathogens. Synthetic molecules can be produced using directed chemical synthesis, combinatorial chemistry or biological methods (e.g. phage display) followed by screening, as is know to those skilled in the art. Depending on the complexity of the library of products generated using a combinatorial method, screening may involve automated, high throughput methods or may utilize a biological selection for identifying the desired ligand. The term "specifically bind" refers to the specific affinity of the reactant for the target pathogen compared to the substantially reduced affinity for other macromolecules, pathogens or cells.

As indicated above, the present invention relates to methods of using HDM to separate or isolate target pathogens by gravity sedimentation, using coated microparticles, coupled to a reactant, preferably an antibody, and used to specifically remove or isolate certain targeted pathogens such as prions, protozoa, viruses, bacteria, fungi, parasites, and so forth.

The reactant can be directly attached to the HDM by adsorption or by direct chemical bonding such as by means of a covalent reaction, for example as described in Hermanson (1996) *Bioconjugate Techniques* New York: Academic Press. The ligand itself may be directly activated with a variety of chemical functionalities including nucleophilic groups, leaving groups, or electrophilic groups. Activating functional groups include alkyl and acyl halides, amines, sulfhydryls, aldehydes, unsaturated bonds, hydrazides, isocyanates, isothiocyanates, ketones, and other groups known to activate for chemical bonding. Alternatively, the HDM and ligand may be bonded through the use of a small molecule coupling reagent. Non-limiting examples of coupling reagents include carbodiimides, maleimides, N-hydroxysuccinimide esters, bischloroethylamines, bifunctional aldehydes such as glutaraldehyde, anyhydrides and the like. Alternately, the reactant may be coupled to the HDM through affinity binding such as a biotinstreptavidin linkage or coupling, as is well known in the art. Where biotinstreptavidin coupling is preferred, streptavidin can be bound to the microparticles by covalent or non-covalent attachment and the biotinylated reactant can be synthesized using methods that are well known in the art. See for example, Hermanson (1996) *Bioconjugate Techniques* New York: Academic Press. Once the reactant is attached to the HDM, the HDM can be added directly to the fluid sample without further dilution or washing steps.

For covalent binding, the HDM may be coated with a polymer that contains chemical moieties or functional groups that are available for covalent attachment to a suitable reactant, typically through a linker. For example, the amino acid polymers described above may have groups, such as the $\epsilon$-amino group of lysine, available to couple the reactant covalently via appropriate linkers.

The invention also contemplates placing a second coating on the microparticles to provide for these functional groups. Functional groups by which the reactant can be attached to the microparticles, are well known in the art and include all those functional groups known to be useful for attaching nucleic acids to solid supports. These include, by way of illustration and not limitation, amino, hydroxyl, carboxyl, aldehyde and sulfhydryl groups. The available functional groups may be further modified to create new functionality. For instance, carboxylates may be converted to primary amines using diamines such as ethylene diamine; carbohydrates and other biological moieties containing polysaccharides may be functionalized to contain aldehyde groups by periodate oxidation; amines may be reacted with 2-iminothiolane to form sulfhydryl groups; hydroxyl groups may be converted to carboxylate moieties using chloroacetic acid. These methods are but a small number of the means known to those of skill for creating new functionality on the HDM or coated HDM (Hermanson, supra).

A plurality of dense, relatively heavy microparticles having the appropriate reactant bound thereto are mixed with the biological fluid sample. The HDM capture the target pathogen rapidly and are then allowed to differentially settle by gravity thus separating the target pathogen(s) from the remainder of the reaction mixture. One advantage of the instant invention is that the methods described herein are particularly adaptable to automation since both the mixing and settling steps can be easily automated. Automation is particularly desirable when the methods of the invention are used in diagnostic applications.

Methods

One embodiment of the method of the invention is a method of removing at least one target pathogen from a biological fluid sample. This method can be used to remove more than one population of target pathogens, and they can be removed sequentially or all at one time. The method comprises the following steps: (a) providing a plurality of high density microparticles having bound thereto a reactant which specifically binds to at least one population of target pathogens and having a density sufficient to provide differential gravity settling of the target pathogen from the sample; (b) mixing a portion of the sample with the microparticles to bind the microparticles to the target pathogen; (c) settling the microparticles with the bound pathogen in the sample to produce a supematant substantially free from the bound pathogen, where the settling is accomplished primarily by gravity; and (d) separating the microparticles bound to the pathogen from the supernatant.

The method of the invention also contemplates pretreating the sample by lysis, for example by the addition of lysis buffers.

Mixing Step

The mixing can be effected by passing the microparticles at least once through the sample, such as by gravity. In this manner, the mixing and settling are conducted simultaneously such that mixing is effected solely by differential gravity settling. Therefore, in one embodiment, the method can be performed without any additional mixing step, instead relying only on the microparticles movement though the sample by gravity. When the mixing and settling steps are combined, this mixing/settling will typically take about 1–5 minutes.

The mixing can, however, also be enhanced by causing the microparticles to repeatedly pass or settle through a substantial portion of the sample. For small volumes, on the order of microliters (typically less than 0.5 milliliter), the mixing can be rapid such as by vortexing or "nutation" such as is described in Coulter, et al., U.S. Pat. No. 5,238,812, which is incorporated herein by reference. For larger volumes, on the order of greater than or equal to 0.5 milliliters (typically 0.5 ml to 3 liters), mixing can also be achieved by gently tumbling the microparticles and the sample in an end over end fashion such as is described in Coulter, et at., U.S. Pat. No. 5,576,185, which is incorporated herein by reference. Such tumbling can be accomplished, for example, by means of a device configured to hold a test tube or other configuration of a reaction vessel, and which slowly rotates the test tube or vessel end over end. When a separate mixing and settling step are utilized, the mixing step will typically take about 15 seconds to 5 minutes, and the settling step is usually carried out for about 1–4 minutes.

Settling Step

As noted above, the settling aspect of the methods of the invention can be performed relying solely on gravity sedimentation. However, for certain applications, it may be desirable to modify the method to accelerate this step. In one such modification, the HDM and sample are briefly spun in a centrifuge to accelerate the settling step.

Separation Step

Separation of the resulting supernatant can be done by numerous methods that are well known in the art such as decanting or siphoning the supernatant, thus leaving the HDM at the bottom of the reaction vessel. For separation of HDM from blood components or other biological fluids, a device commonly referred to as a "plasma extractor" may be used to separate HDM from the fluid if a flexible plastic container is used. Automated versions of plasma extractors may also be used.

When the supernatant is intended for therapeutic use, such as by being transplanted in a human, or where for other reasons it is desired to prevent carry over of particles, it may be desirable to use HDM that are comprised of a magnetic material such as nickel. In this manner, a magnet or magnetic field can be applied to the bottom of the reaction vessel after the HDM have settled, to ensure that the HDM are not removed with the supernatant in the separation step.

The HDM may also be of a sufficient size that they can be differentially filtered to separate them from the biological fluid. When the fluid is a non-cellular product, for instance blood plasma, the HDM may have a wide range of sizes. When the fluid contains cells that are desired for later use, the HDM must be sufficiently larger than the cells so that the microparticles can be differentially filtered from the cell suspension. Preferably the HDM in this circumstance have a diameter of at least 7 microns, and more preferably they are 10 microns or greater in diameter in order to be filtered away from the desired cells.

In one embodiment of the invention, the method is used to remove pathogens from a cell preparation, the supernatant of which can be used for clinical transfusion or transplantation, research or diagnostic applications. In a preferred embodiment, the resulting supernatant, substantially free of the contaminating pathogens, is used therapeutically, either in clinical transfusion or transplantation.

Devices for Performing the Methods of the Invention

The methods of the invention for removing at least one population of target pathogens from a biological fluid sample, can be accomplished using separation devices and components as are well known in the art. For example, the cell separation apparatus described in Coulter, et al., U.S. Pat. No. 5,576,185, can be readily adapted for use with the methods described herein. In general, the method of the invention can be practiced using a device that comprises: (a) a plurality of HDM which (i) have bound thereto a reactant which specifically binds to the target pathogen, (ii) have a density sufficient to provide differential gravity settling of the target pathogen from the sample, and (iii) are capable of settling with the bound pathogen in the sample to produce a supernatant that is substantially free from the bound pathogen, where the settling is accomplished primarily by gravity; (b) a means for mixing a portion of the sample with the HDM to bind the HDM to the target pathogen; and (c) a means for separating the HDM bound to the pathogen from the supernatant.

Suitable devices would include the biological sample containing the target pathogens and a source of the HDM, along with a container in which the sample and HDM can be mixed and subsequently settle. The device may also include a source of the biological sample, for example a blood donor or a container containing a unit of whole blood or a blood component. The sample can be transferred by tubing to a container such as a primary collection container. This primary collection container is sterile and either holds the HDM or is connected to a second container holding the HDM. Accordingly, the HDM can be added to the primary collection container either before, during or after the transfer of the sample into the container.

After the HDM are dispersed through the sample or have been mixed with the sample, the HDM are allowed to settle to the bottom of the container. The device may also include an expressor that allows for removal of the treated sample from the HDM bound to the target pathogen. The expresser can serve to compress the container thereby reducing its volume and forcing the sample, with the pathogens removed, out of the container. Typically the sample is expressed through a tube to another container, while the HDM with bound target pathogen will generally be retained at the bottom of the container due to their greater density.

The containers used in the methods of the invention, as well as in any devices designed for use with these methods, will be determined by the sample size and can be small, such as a 10 microliter container (e.g., a test tube) or large, such as a 100 milliliter to 3 liter container (e.g., a blood bag). In one embodiment, the containers are sterile and formed from flexible plastic sheeting that is biocompatible with the blood or blood components, such as polyvinyl chloride or polyethylene or other materials known to those skilled in the art of making blood storage containers.

The sample container, the HDM as well as other components of the apparatus that contact the sample directly can be sterilized by controlled heat, ethylene oxide gas or by radiation. The preferred method of sterilization will be selected by one skilled in the art to preserve the activity of the HDM, particularly the reactant bound thereto, and will be dependent on the physical characteristics, composition and number of HDM. Preferred sterilization methods will also depend on whether the device is "dry," that is lacking a solution component, or "wet." Alternatively, it is well known to those skilled in the art of making sample (e.g., blood) storage containers that individual incompatible components can be separately sterilized by different means and then joined via a sterile connection process that connects two devices via sterile tubing leads. The preferred method of sterilization will be a terminal sterilization at the 10-6 Sterility Assurance Level in order to enable extended storage of the sample after processing in the apparatus.

The apparatus may optionally include a secondary means for insuring the separation of the sample from the HDM with bound target pathogen. The purpose of the secondary capture step is to further reduce the probability that HDM will be found in the treated sample, which is of particular concern when the final processed sample is a blood component(s). The nature of this secondary capture will take advantage of specific properties of the HDM. When HDM are used that are made of or incorporate a magnetized or paramagnetic substance, the device may include a magnet or a magnetic field, positioned such that it can be applied to the bottom of the container to either accelerate settling or to insure complete that the HDM are not removed during separation step, in particular when the treated sample is to be reinserted into a living organism, such as the human body. The expressor may also be used in combination with the magnet, or if the container is more rigid, the container may be rotated with the magnet held at the bottom, to allow the treated sample to pour or drain. Alternately, the magnet or a magnetic field can be positioned such that the sample can be passed by or through a magnetic field after it is separated from the HDM, but before it is reinserted into the body. This will also serve to insure that no HDM remain in the sample.

The device can also include an optional secondary means of retaining the HDM during the decanting process, which relies on the size or rigidity of the HDM relative to the sample. If the more rigid HDM are large relative to the red blood cell, for example 10 microns in diameter or greater, they may be retained by a sizing filter placed at the outlet of the container. In particular since red blood cells are known to be highly flexible, the size differential to achieve the separation of the more rigid particles may not need to be large, i.e. the HDM and the red blood cells may in fact be of comparable size.

Another optional secondary means of retaining the particles is to compact the HDM by centrifugation after settling. In this manner, the device may include a centrifuge. The device may include a means for briefly spinning the container, if it is desired to accelerate the settling of the HDM. This could be a centrifuge and would operate simultaneous with settling. In this manner, centrifugation would serve to enhance the rate at which the HDM settle and would also lead to enhanced compaction of the HDM with bound pathogen at the bottom of the container The device can be automated such that the sample and HDM are automatically mixed and then moved between the stations or the device can require manual steps that would be carried out by an operator or can be a combination of the two procedures.

For use of the method of the invention in a large scale, such as in an industrial setting, the HDM can be utilized in a large reaction vessel or fluidized bed reactor or as part of a flow process involving column fractionation.

Kits

Another embodiment of the invention is a kit containing a plurality of HDM having bound thereto a reactant which specifically binds to a target pathogen of interest, in combination with instructions for using said microparticles in a method of removing a pathogen of interest from a biological fluid sample. The HDM have a density within the range of 7–10 g/cm$^3$ and may optionally be lyophilized to improve stability during storage. HDM could be packaged integral to a sterile disposable for processing the biological fluid. Formulations of HDM include liquid suspensions, or lyophilized or powdered HDM. Liquid formulations may be stored at a temperature between −15 to 15° C., preferably at 2–8° C., and most preferably can be stored at ambient temperature. Alternatively, the kit could comprise a separate container of HDM, such as a vial, with appropriate means for attaching to commercially available disposable fluid containment sets. Vials may be made of glass or polypropylene. Means of attachment include aseptic spiking and sterile connection using any number of commercially available systems.

As discussed above, it is often desirable to remove or separate the pathogens from a biological fluid sample. Such instructions may indicate that a plurality of HDM, attached to a suitable reactant, are to be mixed with the sample. The HDM, with the target pathogen(s) bound thereto, are then allowed to differentially settle by gravity and the remaining sample is removed. One such application of this kit is for therapeutic uses, where the fluid sample that has been purged of pathogens, is to be reinserted or transplanted into a living organism, such as the human body. In such a case, as well as in all applications described herein, it may be preferable to use HDM that have magnetic properties so that a magnetic field can be used after completion of the gravity settling step, to further insure that all the HDM are removed from the sample.

The general methods of the invention are best understood with reference to the following examples which are intended to enable those skilled in the art to understand more clearly and to practice the present invention. These examples are not intended, nor are they to be construed, as limiting the scope of the invention, but merely are illustrative and representative thereof.

EXAMPLE 1

Coating of High Density Microparticles

Nickel microparticles having a particle size distribution range from about 1 micron to about 25 microns are baked at 250° C. for 5 hours. 1 mg of a tri-amino acid polymer (TAAP) of poly (glutamate, lysine, tyrosine), which is a linear random polymer of the amino acids glutamic acid, lysine, and tyrosine in a ratio 6 parts glutamic acid, 3 parts lysine, and one part tyrosine (Sigma-Aldrich Corporation, Product No. P8854) per 1 gram of nickel in phosphate buffered saline (PBS) is added to the nickel. The TAAP and nickel are incubated with mixing for 1 hour to provide for binding of the TAAP to the nickel microparticles. The microparticles then are washed there times with PBS in order to remove unbound TTAP. 1% glutaraldehyde in PBS then is added, and the microparticles are incubated with mixing for 30 minutes. The particles then are washed three times with PBS.

A desired monoclonal antibody then is added in buffered solution in an amount of 0.75 mg per 1 gram of nickel. The monoclonal antibody and microparticles then are incubated with mixing for 2 hours, and then the microparticles are washed three times with PBS. Glutaraldehyde bonds then are reduced with sodium borohydride. The microparticles then are washed three times with a final buffer of 50 mM Hepes and 50 mM NaCl, pH 7.2.

EXAMPLE 2

The biological fluid sample is a solution of albumin that contains prions, the removal of which is desired. The HDM, coated with a tri-amino acid polymer poly(glutamate, lysine, tyrosine) [6:3:1], as described in Example 1, are conjugated to monoclonal antibody 3F4 specific for human PrP (Kascsack, et at., U.S. Pat. No. 4,806,627). A plurality of the HDM and at least a portion of the sample are combined into a reaction vessel. Once combined, the sample and HDM come into contact with each other and the HDM, now bound to the prions, are allowed to settle differentially by gravity sedimentation. The contact time is very rapid, on the order of minutes. After the HDM have been allowed to separate by differential gravity to the bottom of the reaction vessel, the remaining sample can be separated. An aliquot of the fluid is assayed before and after treatment with the HDM by titration in transgenic mice possessing the human PrP protein (Prusiner, et al., *Cell* 63(4):673–686, 1990). The titer of the prion agent is shown to be reduced by removal with HDM.

EXAMPLE 3

The biological fluid sample is a sample of plasma that contains Hepatitis A virus (strain HM-175; American Type Culture Collection) the removal of which is desired. The HDM, coated with tn-amino acid polymer poly(glutamate, lysine, tyrosine) [6:3:1], as described in Example 1, are conjugated to the monoclonal antibody 7E7 directed against Hepatitis A virus (American Research Products, Belmont Mass.). A plurality of the HDM and at least a portion of the sample are combined into a reaction vessel. Once combined, the sample and HDM are mixed to provide for repeated settling of the HDM in such a manner so as to maximize contact between the HDM and the virus present in the sample. This mixing is accomplished by gently tumbling the HDM and the sample in an end over end fashion such as is described in Coulter, et at., U.S. Pat. No. 5,576,185. As the sample and HDM come into contact with each other, the HDM, now bound to the virus, are allowed to differentially settle by gravity sedimentation. The contact time is very rapid, on the order of minutes. After the HDM have been mixed with the sample and allowed to separate by differential gravity to the bottom of the reaction vessel, the remaining sample can be separated. An aliquot of the plasma supematant is assayed before and after treatment with the HDM by plaquing the virus in FRhK cells, as described in Cromeans, et at., *J. Virol.* 22:45–56 (1987). The titer of the virus is shown to be reduced by removal with HDM.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of removing at least one population of target pathogens from a biological fluid sample, comprising:
   (a) providing a plurality of high density microparticles having bound thereto a reactant which specifically binds to the target pathogen, and having a density sufficient to provide differential gravity settling of the target pathogen from the sample;
   (b) mixing a portion of the sample with the microparticles to bind the microparticles to the target pathogen;
   (c) settling the microparticles with the bound pathogen in the sample to produce a supernatant substantially free from the bound pathogen, where the settling is accomplished primarily by gravity; and
   (d) separating the microparticles bound to the pathogen from the supernatant.

2. The method of claim 1 wherein said mixing is effected by passing the microparticles at least once through the sample.

3. The method of claim 2 wherein said mixing and settling steps are conducted simultaneously such that mixing is effected solely by differential gravity settling.

4. The method of claim 2 wherein said mixing is effected by causing the microparticles to repeatedly settle through a substantial portion of the sample.

5. The method of claim 4 wherein said mixing is effected by vortexing or nutation.

6. The method of claim 4 wherein said mixing is effected by tumbling the sample and the microparticles end-over-end.

7. The method of claim 1 which further comprises spinning the microparticles and sample to accelerate the settling step.

8. The method of claim 1, wherein said microparticles are magnetic and said method further comprises applying a magnet or magnetic field to the sample and microparticles after the settling step.

9. The method of claim 1 wherein more than one population of pathogens are removed sequentially or all at one time.

10. The method of claim 1 wherein the reactant is an antibody.

11. The method of claim 1 wherein the reactant is bound covalently to the microparticles.

12. The method of claim 1 wherein the reactant is bound to the microparticles by streptavidin-biotin coupling.

13. The method of claim 1 wherein said microparticles are formed of nickel.

14. The method of claim 1 wherein said microparticles have a diameter of 1 to 50 microns.

15. The method of claim 1 wherein said microparticles have a diameter of 3 to 35 microns.

16. The method of claim 1 wherein said biological fluid sample comprises non-target materials and the microparticles are 2 to 3 times more dense than said non-target materials.

17. The method of claim 15 wherein said microparticles have a density greater than 2 g/cm$^3$.

18. The method of claim 16 wherein said microparticles have a density of 9 gm/cm$^3$.

19. The method of claim 1 wherein the biological fluid sample is dispersed tissue, bone marrow aspirates or vertebral body bone marrow.

20. The method of claim 18 wherein the supernatant is used for clinical transplantation.

21. The method of claim 1 wherein the volume of the fluid sample ranges from 100 milliliters to 3 liters.

22. The method of claim 1 wherein the target pathogen is a prion.

23. The method of claim 1 wherein the target pathogen is a virus.

24. The method of claim 1 wherein the target pathogen is a bacterium.

25. The method of claim 24 wherein the bacterium is *Bacillus anthracis*.

26. The method of claim 24 wherein the bacterium is *Yersinia pestis*.

27. The method of claim 24 wherein the bacterium is *Francisella tularensis*.

28. The method of claim 1 wherein said microparticles are coated with a poly (glutamic acid, lysine, tyrosine) tri-amino acid polymer, wherein said glutamic acid, said lysine, and said tyrosine are present in said tri-amino acid polymer at a ratio of glutamic acid to lysine to tyrosine of 6:3:1.

* * * * *

UNITED STATES PATENT AND TRADEMARK OFFICE
CERTIFICATE OF CORRECTION

PATENT NO. : 6,730,230 B2
DATED : May 4, 2004
INVENTOR(S) : Cook et al.

It is certified that error appears in the above-identified patent and that said Letters Patent is hereby corrected as shown below:

Column 4,
Line 18, before "candida" delete "such as such as" and insert -- such as --

Column 7,
Line 36, after "is" and before "to" delete "know" and insert -- known --

Column 8,
Line 64, after "a" and before "substantially" delete "supermatant" and insert -- supernatant --

Column 11,
Line 59, after "container" and before "The" insert -- . -- and start a new paragraph beginning with "The device can be"

Column 12,
Line 60, after "washed" and before "times" delete "there" and insert -- three --

Column 13,
Line 54, after "Cromeans," and before "*J. Virol.*" delete "et at.," and insert -- et al. --

Signed and Sealed this

Ninth Day of November, 2004

JON W. DUDAS
*Director of the United States Patent and Trademark Office*